United States Patent [19]

MacKay et al.

[11] 4,015,980
[45] Apr. 5, 1977

[54] USE OF FLUORINATED β-DIKETONES IN THE SOLVENT EXTRACTION OF ZINC

[75] Inventors: Kenneth D. MacKay, Circle Pines, Minn.; R. Brantley Sudderth, Tucson, Ariz.

[73] Assignee: General Mills Chemicals, Inc., Minneapolis, Minn.

[22] Filed: Aug. 4, 1975

[21] Appl. No.: 601,765

[52] U.S. Cl. .............................. 75/120; 75/101 BE; 423/100
[51] Int. Cl.² .................................. C22B 19/26
[58] Field of Search .............. 75/101 BE, 120; 423/100

[56] References Cited
UNITED STATES PATENTS

| | | | |
|---|---|---|---|
| 3,451,807 | 6/1969 | Scribner | 75/117 |
| 3,700,416 | 10/1972 | Lucid | 75/101 BE |

Primary Examiner—G. Ozaki
Attorney, Agent, or Firm—Gene O. Enockson; Patrick J. Span

[57] ABSTRACT

Zinc is extracted from aqueous ammoniacal solutions using fluorinated β-diketones of the structure

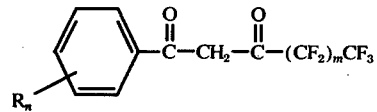

where $n$ is a whole integer of 1 to 4, $m$ is 0, 1 or 2 and R is an alkyl group of 1–25 carbons, the R group or groups providing requisite solubility in liquid hydrocarbon solvents.

6 Claims, No Drawings

USE OF FLUORINATED β-DIKETONES IN THE SOLVENT EXTRACTION OF ZINC

The present invention relates to the extraction of zinc from aqueous ammoniacal solutions thereof using certain fluorinated β-diketones.

A variety of β-diketones have been suggested as being useful for the extraction of specific metal values from their aqueous solutions. Included are fluorinated β-diketones which have been suggested for the extraction of zirconium (U.S. Pat. No. 2,892,681), actinide elements (U.S. Pat. No. 2,894,805), plutonium (U.S. Pat. No. 2,916,349), actinium (U.S. Pat. No. 2,632,763), neptunium (U.S. Pat. No. 2,830,066) vanadium (U.S. Pats. Nos. 3,647,712; 3,700,416; and 3,764,274), lithium (U.S. Pat. No. 3,793,433) and copper (U.S. Pat. No. 3,742,062). Also U.S. Pat. No. 3,451,807 discloses that metals of the Groups II-A, II-B and III-B, copper(II), lead(II), chromium(III), iron(III), cobalt(II), nickel(II) and manganese(II) are extracted by the use of trifluoroacetylacetone in an alkalol of 4–8 carbon atoms.

Zinc is a very difficult metal to complex and recover out of its dilute aqueous solutions. While the above mentioned U.S. Pat. No. 3,451,807 describes extraction of zinc, such extraction was at pH's of 2.6–8.0 with no ammonia present. Furthermore, the diluent used in the said specific example was butanol which is an inflammable, volatile solvent with substantial water solubility (9 g./100 g. $H_1O$). Such system therefore has potentially only limited commercial value in large scale operations due to the difficulty in handling the alkanol solvent and the expense in the loss thereof to the dilute aqueous solutions.

We have now discovered that zinc can be recovered from its dilute aqueous ammoniacal solutions by using fluorinated μ-diketones of the following formula

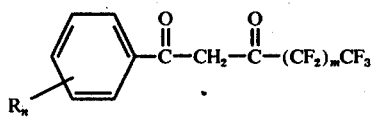

where $n$ is a whole integer of 1–4, $m$ is 0 1 or 2 and R is an alkyl group of 1–25 carbon atoms with the proviso that $R_n$ must provide solubility properties sufficient for the diketones and the resulting zinc complexes to be soluble at a level of at least 2% by weight in essentially water immiscible liquid hydrocarbon solvents. Preferably R will be branched chain and contain 8 or more carbon atoms when $n$ is 1. Especially preferred compounds are those wherein R is a branched chain dodecyl group in the para position.

In the extraction recovery process of our invention, the described fluorinated β-diketones are dissolved in the said liquid hydrocarbon solvent and the resulting solution is contacted with the aqueous ammoniacal zinc containing solution to form a complex of the β-diketone and the zinc in the organic phase. Such phase is then separated from the aqueous phase and the zinc values are stripped from the organic phase.

The solvents are essentially water immiscible and are preferably aliphatic or aromatic hydrocarbons such as the petroleum derived liquid hydrocarbons including kerosene, fuel oil, etc. Kerosene is in wide use in the liquid ion exchange recovery of metal values and is the currently preferred solvent. In addition to the simple hydrocarbon solvents, chlorinated hydrocarbons may also be used. Accordingly, both the unsubstituted and the chlorinated solvents are contemplated by the term "liquid hydrocarbon".

In the process of our invention, the fluorinated β-diketones as described are dissolved in the solvent in an amount sufficient to extract at least a portion of the zinc values from the aqueous ammoniacal solution thereof. Preferably, the said diketones will be used in amounts of about 2 to 15% by weight based on the weight of the solvent.

The ammoniacal zinc containing solutions have pH's above 7.0 and preferably in the range of 7.0 to about 10.0. Such solutions can contain various amounts of recoverable zinc but commercially, the process is particularly attractive when the zinc concentrations are in the range of 1 to 50 g. Zn. $^{++}$/liter. The ammonia concentration varies as the operating pH is normally at that level used in the ore leaching to arrive at the zinc containing ammoniacal solution.

The phase ratios can vary widely since the contacting of any quantity of the fluorinated β-diketone solution with the zinc containing aqueous phase will result in extraction of zinc values into the organic phase. However, for commercial practicality, the organic:aqueous phase ratios are preferably in the range of 10:1 to 1:10. Also for practical purposes, the extractions (and stripping) are normally carried out at ambient temperatures and pressures. The entire process can be carried out continuously with the stripped organic phase being recycled for contacting further quantities of zinc containing solutions.

The loaded organic is preferably stripped using aqueous acid stripping mediums such as aqueous sulfuric acid (i.e. pH of about 3.0 or lower or approximately 0.5 to 200 g./l. $H_2SO_4$). The zinc is then desirably recovered from the aqueous stripping medium by electrolysis. The loaded organic:aqueous stripping phase ratios can also vary widely. However, the over-all object of the precess is to provide a zinc containing solution wherein the zinc is present in higher concentrations than in the starting aqueous solution. Accordingly, the loaded organic:aqueous stripping phase ratio will preferably be in the range of 20:1 to 1:20.

Optionally, the loaded organic phase prior to stripping may be subjected to air sparging and/or scrubbing with dilute or weak aqueous acidic solutions to remove ammonia therefrom. The air sparge represents a convenient method for the removal of loosely bound ammonia in the zinc loaded organic solution. The scrub stage is also used to selectively remove ammonia from the said loaded organic phase. The desirability of including either or both of the above steps will depend somewhat on the commercial application and particularly the make-up of the starting aqueous ammoniacal zinc containing solution.

The following Examples illustrate preferred embodiments of the invention without being limiting:

EXAMPLE I

Part A — β-Diketone Reagent Preparation

A dispersion of 84.5 g. (2 moles) of 57% sodium hydride in mineral oil was slurried with n-pentane and the supernatant was removed by suction through a sintered glass dip tube. The process was repeated three times before 500 ml. of ethyl ether was added at once. The mixture was slurried and 284 g. (2 moles) of ethyltrifluoroacetate was rapidly added. Then about 2 ml. of dodecylacetophenone (the dodecyl group is branched chain and was derived from a synthetic alkylbenzene — Chevron alkylate 21 — in which the alkyl chain is branched and contains an average of 12 carbon atoms) was added to the slurry and gas evolution occurred immediately as evidenced on a wet test meter. Two hundred eighty eight grams (about 1 mole) of the dodecyl acetophenone was diluted with 500 ml. of ethyl ether and added to the reaction mixture at such a rate as to maintain reflux. The time of addition was three hours. When the addition was complete, the mixture was stirred another 30 minutes at which time gas evolution had ceased. Another 500 ml. of ethyl ether was added and the excess sodium hydride was neutralized by the slow addition of absolute alcohol, then a small amount of water. When the sodium hydride failed to react, the mixture was poured onto a mixture of ice and hydrochloric acid with vigorous stirring. The phases then were separated and the upper organic layer was washed twice with water. After drying over anhydrous magnesium sulfate, the solvent was distilled under reduced pressure. There was obtained 372.6 g. of β-diketone reagent (distilled at 135–55° C. — 0.3–0.4 mm.Hg.) having the formula:

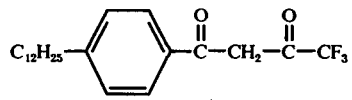

Part B — Zinc Extractions - Varying Phase Ratios

A series of extractions were carried out with the fluorinated β-diketone prepared in Part A. In these extractions, a 10% wt./vol. solution of the β-diketone in Napoleum 470 (an aliphatic kerosene having a flashpoint of 175° F., boiling point >400° F. — available from Kerr-McGee) was prepared. Portions of this solution were shaken for 60 minutes (at room temperature) in separatory funnels with portions of an aqueous solution containing 11.75 g./l. $Zn^{++}$ as $ZnSO_4$, 10 g./l. $NH_3$ and 188 g./l. $(NH_4)_2SO_4$ at varying phase ratios. The phases were then allowed to separate and analyzed for zinc. The results are set forth in the following Table 1:

Table 1

| O/A Phase Ratio | $Zn^{++}$ (organic) g./l. | $Zn^{++}$ (aqueous) g./l. |
|---|---|---|
| 5/1 | 2.40 | 0.00165 |
| 2/1 | 5.85 | 0.0336 |
| 1/1 | 7.50 | 4.0 |
| 1/2 | 7.10 | 8.75 |

Part C — Rate of Zinc Extraction

Extractions were performed as in Part B except the organic:aqueous phase ratio was 1:1 and samples of the organic and aqueous phases were removed at various time intervals and analyzed for zinc. The results are set forth in the following Table 2:

Table 2

| Time | $Zn^{++}$ (organic) g./l. | $Zn^{++}$ (aqueous) g./l. |
|---|---|---|
| 15 sec. | 8.00 | 4.43 |
| 30 sec. | 8.00 | 4.47 |
| 60 sec. | 7.70 | 4.39 |
| 2 min. | 7.75 | 4.35 |
| 5 min. | 7.75 | 4.32 |
| 10 min. | 7.65 | 4.30 |

Part D — Stripping of Zinc From The Loaded Organic

An organic phase made up as in Parts B and C loaded with 6.6 g./l. $Zn^{++}$ was contacted with shaking at an organic:aqueous stripping medium phase ratio of 1:1 for various time intervals and the phases were analyzed for zinc. The stripping medium was aqueous $H_2SO_4$ (50 g./l.). The results are set forth in the following Table 3:

Table 3

| Time | $Zn^{++}$ (organic) g./l. | $Zn^{++}$ (aqueous) g./l. |
|---|---|---|
| 15 sec. | 1.48 | 5.35 |
| 30 sec. | 0.30 | 6.06 |
| 60 sec. | 0.0040 | 6.58 |
| 2 min. | 0.0011 | 6.65 |
| 5 min. | 0.00036 | 6.73 |
| 10 min. | 0.00021 | 6.62 |

EXAMPLE II

Example I, Part B was repeated except using a β-diketone of the structure:

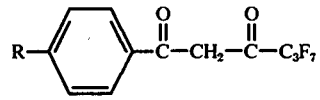

where R is the branched chain dodecyl group. Results were as follows:

Table 4

| O/A Phase Ratio | $Zn^{++}$ (organic) g./l. | $Zn^{++}$ (aqueous) g./l. |
|---|---|---|
| 5/1 | 2.17 | 0.07 |
| 2/1 | 3.19 | 4.70 |
| 1/1 | 3.16 | 8.00 |
| 1/2 | 3.18 | 9.40 |

Likewise, a loaded organic phase of the β-diketone of this Example II (0.8 g./l, $NH_3$ and 3.09 g./l. $Zn^{++}$) was stripped by contacting the same with shaking for one hour with aqueous $H_2SO_4$ (100 g./l.) at an organic-:aqueous stripping medium phase ratio of 1:1. The stripped organic analyzed only 0.0002 g./l $Zn^{++}$.

For comparison purposes, other β-diketones were tested for zinc extraction as set forth in the following Experiments:

EXPERIMENT 1

Example I, Part B was repeated except using a β-diketone of the formula:

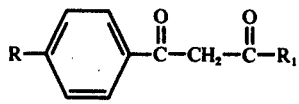

where R is the branched chain dodecyl group and $R_1$ is a branched chain heptyl group. Results are set forth in the following Table 5:

Table 5

| O/A Phase Ratio | $Zn^{++}$ (organic) g./l. | $Zn^{++}$ (aqueous) g./l. |
|---|---|---|
| 5/1 | 0.018 | 12.8 |
| 2/1 | 0.018 | 13.7 |
| 1/1 | 0.018 | 13.2 |
| 1/2 | 0.016 | 12.7 |
| 1/5 | 0.028 | 13.1 |

EXPERIMENT 2

Extractions were also attempted with a 5% wt./vol. solution of trifluoroacetylacetone in Napoleum 470 (same aqueous as used in Example 1). The initial extraction attempt gave gross amounts of precipitate. Addition of 10% isodecanol to the organic failed to improve solubility of the zinc complex. Further, the zinc concentration remaining in the aqueous phase after extraction was about five times greater for trifluoroacetylacetone than the β-diketone used in Example I. At the same time, the molar concentration of trifluoroacetylacetone was some three times greater.

The embodiments of the invention in which an exclusive property or privilege is claimed are defined as follows:

1. The process of recovering zinc from an aqueous ammoniacal solution thereof which comprises contacting said solution with a solution of a fluorinated β-diketone dissolved in an essentially water immiscible liquid hydrocarbon solvent to extract at least a portion of the zinc into the organic phase, separating the organic phase from the aqueous phase and stripping zinc from the organic phase, said β-diketone having the formula

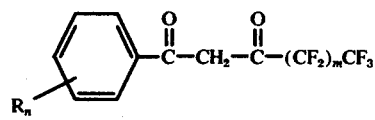

where $n$ is a whole integer of 1 to 4, $m$ is 0, 1 or 2 and R is an alkyl group of 1–25 carbon atoms with the proviso that $R_n$ must provide solubility properties sufficient for the β-diketone and the resulting zinc complex thereof to be soluble at a level of at least 2% by weight in the essentially water immiscible liquid hydrocarbon solvent.

2. The process of claim 1 wherein $m$ is 0.

3. The process of claim 1 wherein $n$ is 1 and the R group is in the para position.

4. The process of claim 3 wherein R contains at least 8 carbon atoms.

5. The process of claim 4 wherein R is a branched chain dodecyl group.

6. The process of claim 1 wherein the β-diketone is present in an amount of about 2 to 15% by weight based on the weight of the solvent.

* * * * *

UNITED STATES PATENT AND TRADEMARK OFFICE
CERTIFICATE OF CORRECTION

PATENT NO. : 4,015,980
DATED : April 5, 1977
INVENTOR(S) : Kenneth D. MacKay, R. Brantley Sudderth It is certified that error appears in the above-identified patent and that said Letters Patent are hereby corrected as shown below:

Column 1, line 32 - Delete "$H_1O$" and insert -- $H_2O$ --.

Column 1, line 39 - Delete " $\mu$-diketones " and insert -- $\beta$-diketones --.

Signed and Sealed this

Fourteenth Day of June 1977

[SEAL]

Attest:

RUTH C. MASON
*Attesting Officer*

C. MARSHALL DANN
*Commissioner of Patents and Trademarks*